United States Patent [19]

Yang

[11] Patent Number: 4,979,123
[45] Date of Patent: Dec. 18, 1990

[54] APPARATUS FOR DETERMINING CONCENTRATIONS OF MINERAL ELEMENTS

[75] Inventor: Keun Y. Yang, Seoul, Rep. of Korea

[73] Assignee: Goldstar Co., Ltd., Seoul, Rep. of Korea

[21] Appl. No.: 199,765

[22] Filed: May 27, 1988

[30] Foreign Application Priority Data

May 30, 1987 [KR] Rep. of Korea ............................ 5527

[51] Int. Cl.$^5$ ............................ G01J 3/44; G01J 3/32; G01J 3/28; G01J 3/06
[52] U.S. Cl. .................................. 364/498; 356/301; 356/328; 356/329
[58] Field of Search ............... 356/300, 301, 302, 303, 356/304, 305, 328, 329; 364/498

[56] References Cited

U.S. PATENT DOCUMENTS

| | | | |
|---|---|---|---|
| 3,229,566 | 1/1966 | Hutchinson et al. | 356/329 |
| 3,846,024 | 11/1974 | Turner | 356/329 |
| 4,191,473 | 3/1980 | Hansch | 356/300 |
| 4,571,074 | 2/1986 | Thevenon | 356/328 X |
| 4,575,241 | 3/1986 | Demers et al. | 356/328 X |
| 4,648,714 | 3/1987 | Benner et al. | 356/301 |
| 4,784,486 | 11/1988 | Van Wagenen et al. | 356/301 |

Primary Examiner—Parshotam S. Lall
Assistant Examiner—Edward R. Cosimano
Attorney, Agent, or Firm—Birch, Stewart, Kolasch & Birch

[57] ABSTRACT

An apparatus for determining concentrations of mineral elements comprising an improved spectrometer wherein the spectrometer functions to diffract the light to be measured by means of a rotary grating and to determine the strength of light by using a single PM tube and further detects the wavelength of the diffracted light, by using a laser beam generator, reflective mirrors, photo diodes so as to analyze the composition and the concentration of mineral elements.

5 Claims, 3 Drawing Sheets

APPARATUS FOR DETERMINING CONCENTRATIONS OF MINERAL ELEMENTS

BACKGROUND OF THE INVENTION

The present invention relates to an apparatus for determining concentrations of mineral elements contained in an alloy. Particularly, the present invention relates to an apparatus for determining concentrations of mineral elements, which is suitable for an analysis of an alloy containing a small amount of mineral elements.

Conventional apparatus for determining concentrations of mineral elements, as shown in FIG. 1 comprises a glow discharge lamp (GDL) 10 adapted to atomize, elements ,consisting a sample S to be determined and excite the atomized elements so as to emit a light L, a spectrometer 20 adapted to diffract said light L emitted from said GDL 1 into various angles and detect the strength of said diffracted lights, a vacuum maintaining device and argon gas-supply system 30 adapted to maintain the interior of the GDL 0 under the vacuum condition and supply argon gas to said interior of the GDL 10, a high voltage supply 40 adapted to apply a high voltage to the GDL 10, an A/D converter and amplifier 50 adapted to amplify the electric signal from the spectrometer 20 and convert it into a digital signal, and a computer 60 adapted to treat said digital signal from said A/D converter and amplifier 50, calcuate the composition and the strength of elements consisting said sample S, and control the concentration-determining apparatus.

The inner space 11 of the GDL 10 is sealed by the sample S and a first window 12. An anode 13 and a cathode 14 to which the high voltage is applied are provided in the GDL 10. The sample S is connected to the cathode 14, so as to function as a cathode. The spectrometer 20 comprises a casing 21 an a second window 22 arranged at a certain part of said casing 21. Through the second window 22, the light L emitted from the GDL 10 passes. In the interior of the casing 21, the spectrometer 20 also includes a focusing lens 23 adapted to focus the light, a grating 24 adapted to diffract said focused light L, a slit plate 27 having an inlet slit 25 positioned at the path of an incident light and a plurality of outlet slits 26 through which said diffracted light from said grating 24, pass and photo multiplier tubes (PM tubes) 28 adapted to determine the strength of the diffracted light which have passed through said outlet slits 26 of the slit plate 27. The outlet slits and the PM tubes 28 are arranged at the path through which among the diffracted lights from the grating 24, several lights of certain wavelengths pass.

Now, the operation of the conventional apparatus for determining concentration of mineral elements will be described in detail.

First, a reference alloy sample S, in which the concentrations of the elements consisting the alloy are known, is attached on the GDL 10, as shown in FIG. 1. By the high voltage supply 40 and the vacuum-maintaining device and argon supply system 30 controlled by the computer 60, the interior of the GDL 10 is maintained under a proper vacuum condition of, for example, about $10-10^{-1}$ Torr, and argon gas is then injected into the interior of the GDL 10. As the high voltage supply 40 applies the high voltage to the interior of the GDL 10, an electric field is established between the anode 13 and the cathode 14. The electric field causes the argon gas to acceleratively flow toward the reference sample S and impact thereupon, so that some atoms of the elements consisting the reference sample S are separated. The atoms of the separated element impact against the electrons formed between two electrodes and the argon gas. In process of this impact, the atoms of the elements absorb an energy and is excited from a ground condition to a high energy the excited states. The excited atoms return from the excited state to the ground state, emitting a light corresponding to the resonance frequency of atoms. This process is continued while the voltage is supplied. Accordingly, the resonance of all elements consisting the reference sample S is discharged from the GDL 10, The discharged light L comes into the spectrometer 20, via the first window 12 attached to the GDL 10 and the second window 22 attached to the spectrometer 20. Thereafter, the light L passes through the focusing lens 23 and the inlet slit 25. Then, the light L is focused on the grating 24. The focused light is diffracted into various angles according to the wavelength. The strength of each light diffracted by the grating 24 is determined by each PM tube 28 which is arranged in the path of light passing through an outlet slit 26.

If the reference sample S contains three elements to be measured, the light L discharged from GDL 10 is mixed with the frequencies $F_1$, $F_2$, and $F_3$ of said elements. This light L is diffracted into three angles by the grating 24 disposed in the spectrometer 20. The three diffracted lights pass through the outlet slits 26, respectively. The three PM tubes determine strengths of the lights which have frequencies $F_1$, $F_2$, and $F_3$, respectively.

Thereafter, the strengths $I_1$, $I_2$, and $I_3$ of the lights determined by the PM tubes 28 are amplified and converted into digital signals by the A/D converter and amplifier 50. The digital signal is memorized in the computer 60. The strengths $I_1$, $I_2$, and $I_3$ memorized in the computer 60 correspond to the known concentrations $C_1$, $C_2$, and $C_3$ of elements, respectively.

After the determination is completed, with regard to the reference sample S, an alloy which contains the same kind of the elements as those of the reference sample, but of unknown concentrations is substituted for the reference sample. As the alloy is treated in the above-mentioned manner relating to the reference sample S, the strengths $I'_1$, $I'_2$, and $I'_3$ corresponding to the respective unknown concentrations $C'_1$, $C'_2$, and $C'_3$ of three elements of the alloy can be received by the computer 60. The computer 60 compares the strengths $I'_1$, $I'_2$, and $I'_3$ with the strengths $I_1$, $I_2$, and $I_3$ and calculates values the respective concentrations $C'_1$, $C'_2$, and $C'_3$ by a software equipped in the computer 60. Thus, the concentrations of the elements to be determined can be found.

However, when several kinds of mineral elements have to be simultaneously analyzed by using the above-mentioned conventional apparatus, the apparatus needs a plurality of expensive PM tubes 28, the number of which corresponds to that of the elements to be measured. This results in the increase of the manufacturing cost. Additionally, it is necessary to provide a complex high voltage circuit and safety device, so as to actuate a plurality of PM tubes 28. In order to increase the resolution of the diffracted lights from the grating 24, the PM tubes 28 are arranged at the position remote from the grating 24, thereby causing the spectrometer 20 to have a large size.

SUMMARY OF THE INVENTION

Therefore, an object of the present invention is to eliminate the above-mentioned disadvantages encountered in the prior art and to provide a compact and inexpensive apparatus for determining the concentrations of mineral elements, through the improvement of a spectrometer which diffract the light to be measured or a rotary grating, determines the strengths of the diffracted lights with only one PM tube, and detects the wave-lengths of the diffracted light, the strengths of which have been determined in the PM tube a laser beam emitting device, a reflective mirror, and photo diodes so as to analyze the composition and the concentrations of the component.

In accordance with the present invention, this object can be accomplished by providing an apparatus for determining concentrations of mineral elements comprising: a glow discharge lamp adapted to atomize elements consisting a sample to be measured and excite the atomized elements to emit a light; a spectrometer adapted to focus said light from said glow discharge tube with a first focusing lens, to diffract the focused light into multiangles, depending upon the frequencies, and to detect the frequencies of said diffracted lights; an A/D converter and amplifier adapted to amplify the electric signal from said spectrometer and convert it into a digital signal and an amplifier to amplify said signal from the spectrometer; a computer adapted to analyze a data from the spectrometer through the A/d converter and amplifier and the amplifier and control said apparatus.

In accordance with one aspect of the present invention, the spectrometer comprises a laser beam generator adapted to emit a laser beam; a second focusing lens adapted to focus said laser beam; a rotary reflective mirror adapted to reflect said laser beam; a rotary polyhedron carrying a said grating and a first reflective mirror on the upper and lower portion of peripheral surface thereof; a drive motor and a drive circuit to rotate said rotary polyhedron at a high rate; a first slit plate having a plurality of slits arranged in a circular shape, said laser beam reflected from said first reflective mirror passing through said first slits; a plurality of first photo diodes, each arranged adjacent to the rear of each corresponding first slit of said slit plate, and adapted to detect the wavelengths of the diffracted light; a slit adapted to indicate the scanning initiating point of said laser beam; and a second photo diode adapted to sense said scanning initiating point.

BRIEF DESCRIPTION OF THE DRAWINGS

The present invention will be better understood after a reading of the following detailed description of the preferred embodiment when taken in conjunction with the accompanying drawings in which;

FIGS. 4 to 7 are views explaining the functions of the spectrometer according to the present invention, in which FIG. 4 is an explanation showing a diffraction of a light by a grating;

FIG. 5 is an explanation showing that a light is diffracted, in the grating into multiple angles according to the wavelengths and that a diffracted light of a certain wavelength reaches a PM tube to be determined the strength of light;

FIG. 6 is a view showing a laser beam-scanning device which detects a wavelength of light corresponding to the strength of the diffracted light determined by a PM tube; and FIGS. 7(A) and 7 (B) are wave diagram of signal generated from first and second photo diodes and the PM tube when a rotary polyhedron rotates with one surface thereof.

DETAILED DESCRIPTION OF THE PREFERRED EMBODIMENTS

Figure 1:
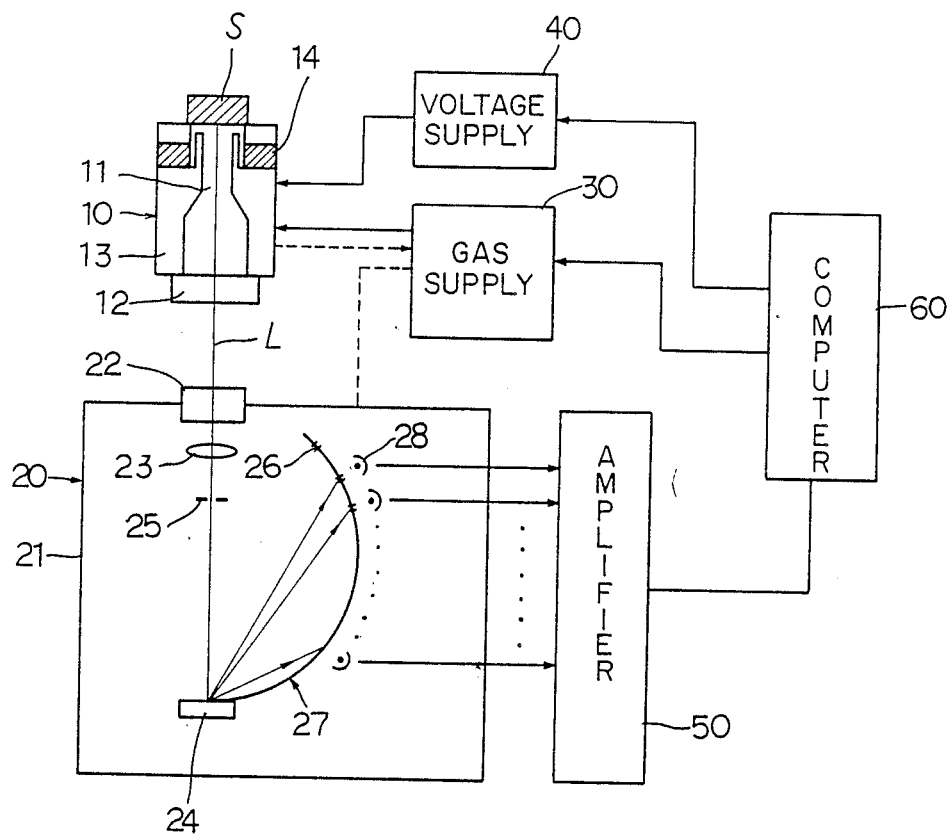
FIG. 1 is a schematic view of a conventional apparatus for determining the concentrations of mineral elements.
Figure 2:
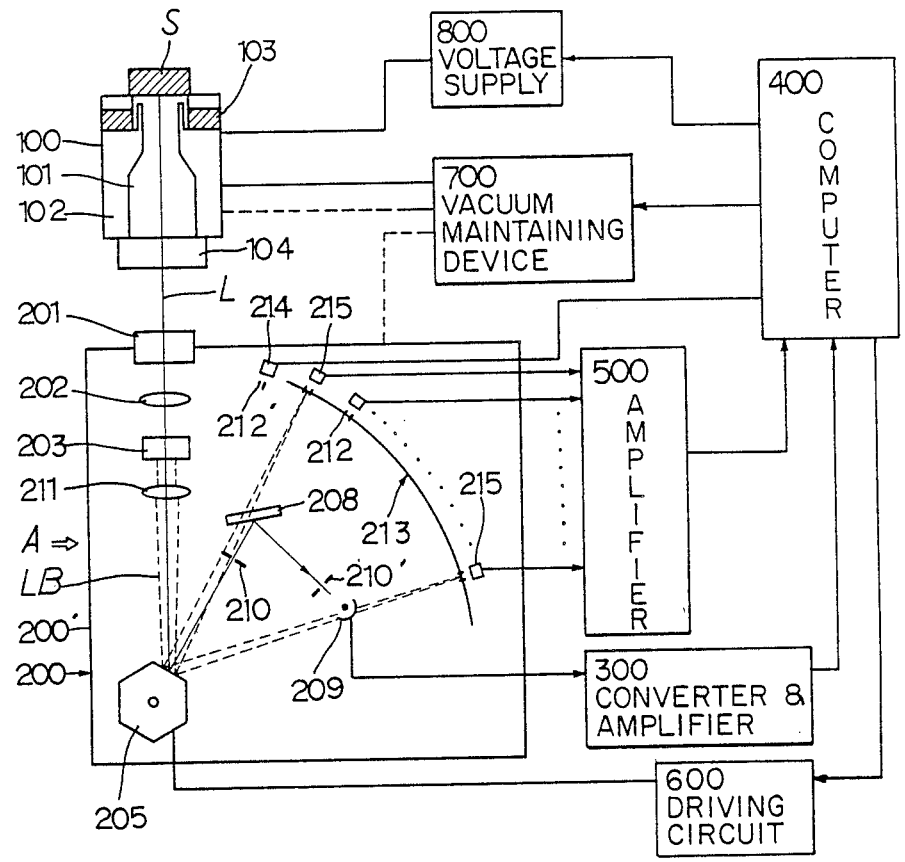
FIG. 2 is a schematic view of an apparatus for determining the concentrations of mineral elements, in accordance with the present invention.
Figure 3:
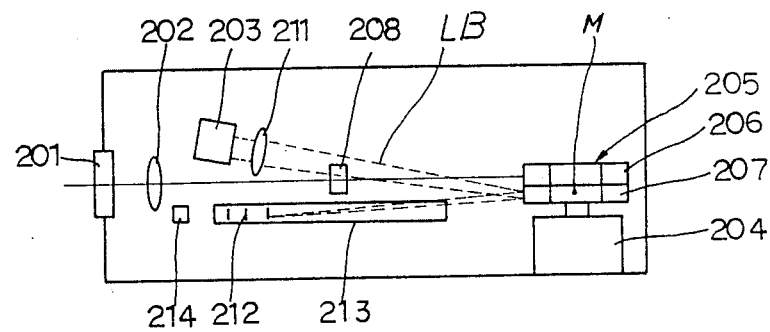
FIG. 3 is a elevation view of an spectrometer shown in FIG. 2 which is taken in the direction A.

Referring to FIGS. 2 and 3, an apparatus for determining the concentrations of mineral elements in accordance with the present invention is shown. In the drawings, the reference numeral "100" designates a glow discharge tube which atomizes samples to be measured and to excite the atomized elements of the samples to emit a light. The reference numeral "200" designates a spectrometer adapted to diffract the light from the glow discharge tube 100 and enters and thus to detect the strength of the diffracted light. The reference numeral "300" designates an A/D converter and amplifier which amplifies the electric signal from the spectrometer 200 and converts it into a digital signal. The reference numeral "400" designates a computer adapted to analyze a data and control the apparatus. The spectrometer 200 comprises a laser beam generator 203 adapted to emit a laser beam LB, a second focusing lens 211 adapted to focus the laser beam LB, a rotary grating 206 adapted to diffract the light L focused by said second focusing lens, a reflective mirror 207 adapted to reflect the laser beam LB, and a rotary polyhedron 205 which carries said grating 206 and second reflective mirror 207 at the upper and lower portion of peripheral surface thereof and rotates at a high rate by the drive force of a drive motor 204. The spectrometer 200 also includes a first reflective mirror 208 adapted to reflect a light diffracted in the rotary grating 206, a single PM tube 209 adapted to detect said reflected light and determine the strength thereof, inlet and outlet slits 210 and 210' arranged both sides of said first reflective mirror 208, respectively, a slit plate 213 having a plurality of slits 212 arranged in a circular shape and a center of curvature positioned between the rotary grating 206 of the rotary ployhedron 205 and the second reflective mirror 207, the laser beam LB reflected from the second reflective mirror 207 entering said slits 212, a plurality of wavelength detecting photo diodes 215 each disposed adjacent each of said slits 212 and adapted to sense a laser beam LB and detect a variable wavelength of the diffracted light, a slit 212' adapted to indicate on initiation of the scanning, and a photo diode 214 for detecting a scanning initiating point. The photo diodes 214 and 215 of the spectrometer 200 are connected to the computer 400, via the amplifier 500. The drive motor 204 is connected to the computer 400, via a driving circuit 600. As the laser beam generator 203, a semiconductor laser is preferably used. The rotary grating 206 is formed, by attaching a hologram grating thereon. The hologram grating can be made by forming an interference pattern on a film by utilizing a holography technique. A light axis of an optical system focusing the laser beam LB is spaced at a certain angle from the other light axis of an optical system focusing the light LB so that the laser beam LB and the path of light L to be measured can not be overlapped with each other.

In the drawings, the reference numeral "700" designates a vacuum-maintaining device and argon supply system adapted to maintain the effective space 101 of the GDL 100 under a proper vacuum condition and supply an argon gas to said space 101 of the GDL 100. The effective space 101 of the GDL 100 is defined by the sample S and the window 104. The reference numeral "800" designates a high voltage supply adapted to apply a high voltage to an anode 102 and a cathode 103 of the GDL 100. These devices are well-known in the technical field. FIG. 3 is a view of spectrometer 200 from the direction indicated by arrow A, wherein M indicates mirror 207.

Figure 4:
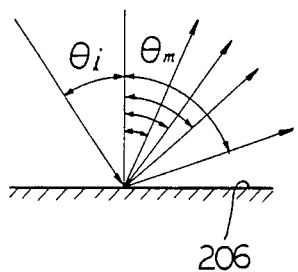

In order to operate the apparatus of the present invention having the above-mentioned construction, a sample which contains elements of known concentrations has to be attached on the GDL 100, and then, the GDL 100 has to be operated, according to the same principle as that of the prior art. As the GDL 100 is actuated, a light L is emitted therefrom. The light L passes through the second window 201 of the spectrometer 200 and the first focusing lens 202. Then, the light L is focused on the rotary grating 206 of the rotary polyhedron 205 which rotates, at a high rate, in clockwise in FIG. 2. The focused light is diffracted into multiple angles according to the wavelengths, as shown in FIG. 4. The diffraction is carried out, according to the following formula:

$$d (\sin \theta i + \sin \theta m) = m\lambda \quad (1)$$

Wherein, d is a groove space of the diffraction, $\theta i$ is an incidence angle at which the light enters the diffraction plate, $\theta m$ is a diffraction angle, m is an order, and $\lambda$ is a wavelength.

Figure 5:
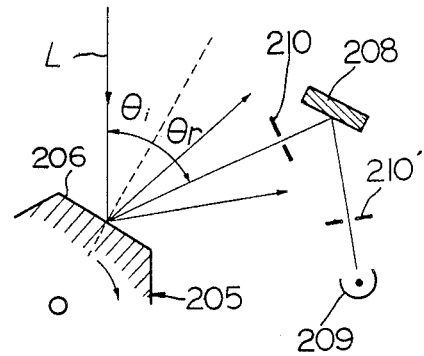

That is, as the light L which has passed through the focusing lens 202 enters the grating 206 of the rotary polyhedron 205 at $\theta i$, it is diffracted at the diffraction angle $\theta m$. From this light, only a diffracted light of wavelength which satisfies the condition $\theta m = \theta i$, in order to pass through the inlet slit 210 can be reflected from the first reflective mirror 208 and detected by the PM tube 209 as shown in FIG. 5. And, FIG. 7(B) shows a waveform diagram of the signals which are generated from the photomultiplier tube 209 and are going to be is applied to the amplifier and A/D converter 300. As the rotary polyhedron 205 rotates, the incidence angle $\theta i$ and the diffraction angle $\theta m$ continuously vary. Accordingly, the wavelength of light which is reflected from the first reflective mirror 208 and detected by the PM tube 209 continuously varies, depending on the rotation angle of the rotary polyhedron 205. Consequently, as $\theta i$ varies by the continued rotation of the rotary polyhedron, 205, the PM tube 209 continuously detects a different light of a different wavelengths of the light.

Figure 6:
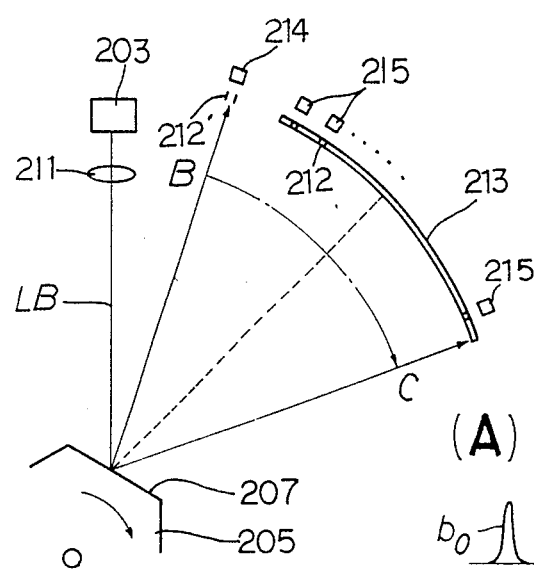

When the light L from the GDL 100 is diffracted in the rotary grating 206 and detected by the PM tube 209, a laser beam LB is emitted from the laser beam generator 203. The laser beam LB enters the second rotary reflective mirror 207 which rotates in clockwise, together with the rotary grating 206. Then, the laser beam is reflected from the reflective mirror 207 and scanned from the direction B to the direction C as shown in FIG. 6. At this time, each second photo diode 214 detects the point at which each surface of the rotary polyhedron 205 initiates the scanning. Each photo diode 215 adapted to analyze the wavelength of light detects the laser beam LB which varies the reflection path thereof, depending upon the rotation of the rotary polyhedron 205.

In the manufacture of the apparatus of the present invention, therefore, the second slits 212 and second photo diodes 215 should be assembled as follows. That is, the assembly should be carried out so that at the rotation angle of the rotary polyhedron 205 detected by the PM tube 209, the light having a wavelength corresponding to an element to be measured passes through the path of the laser beam LB reflected from the second reflective mirror 207. In this case, the PM tube 209 can detect the diffracted light having a wavelength corresponding to an element to be measured and a selected photo diode 215 can detect a laser beam reflected at the same rotation angle of the rotary reflective polyhedron 205. Thus, it is possible to find an element corresponding to the diffracted light in which the strength thereof is detected by the PM tube 209.

Figure 7:
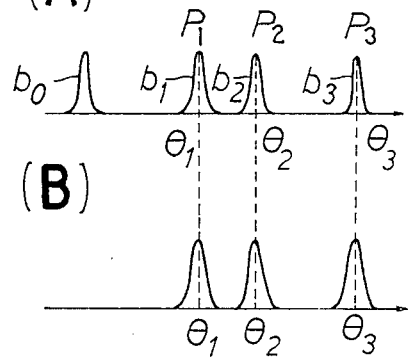

For example, assume that there are three elements to be determined in an alloy. Then, it is possible to calculate, by the formula (1), angles $\theta_1$, $\theta_2$, and $\theta_3$ of the rotary polyhedron 205 at which respective frequencies $F_1$, $F_2$, and $F_3$ of the above-mentioned elements are detected by the PM tube 209, via the rotary grating 206. By the reflection law of the light it is also possible to find positions $P_1$, $P_2$, and $P_3$ at which the laser beam reflected from the second reflective mirror 207 of the rotary polyhedron 205 is focused. The photo diodes 215 should be disposed at the focusing positions $P_1$, $P_2$, and $P_3$, respectively. When a reference sample S containing three elements of known concentrations is attached on the GDL 100, and this GDL 100 is then actuated, a light L is emitted from the GDL 100 as above-mentioned. According to the above-mentioned arrangement, the light L passes the second window 201 and the focusing lens 202, then enters the rotary grating 206 of the rotary polyhedron 205, and then is diffracted therein. As the laser beam LB is scanned from the direction B to the direction C, a signal $b_0$ indicating the initiation of the scanning of laser beam is generated from the first photo diode 214 at each surface of the rotary polyhedron 205, as shown in FIG. 7 (A). The second photo diodes 215 generate signals $b_1$, $b_2$, and $b_3$ which are detected at the rotation angles $\theta_1, \theta_2$, and $\Theta_3$ of the element rotary polyhedron 205, respectively. At the same angles $\theta_1$, $\theta_2$, and $\theta_3$, the frequencies $F_1$, $F_2$ and $F_3$ of light corresponding three elements are detected by the PM tube 209 so that respective strengths $I_1$, $I_2$, and $I_3$ of elements can be determined.

If the PM tube 209 could not detect any signal at a rotation angle $\theta_2$ of the rotary polyhedron, this means that the reference sample S does not contain an element of the frequency $F_2$. If the rotary polyhedron 205 has N surfaces and rotates m cycles per one determination, the first photo diode 214 and totally sends $m \times N$ signals to the computer 400. The PM tube 209 detects $m \times N$ strengths per each element and the computer 400 averages these values. Thus, the averages $\bar{I}_1$, $\bar{I}_2$, and $\bar{I}^3$ corresponding to the elements of the frequencies $F_1$, $F_2$, and $F_3$, respectively, can be calculated. The calculated values are recorded in the computer 400 as values of the known concentrations $C_1$, $C_2$, and $C_3$ of elements.

After the determination is completed with regard to the reference sample S, an alloy which contains the same kinds of the elements as those of the reference sample, but having unknown concentrations is substituted for the reference sample S. As the alloy is treated in the above-mentioned manner relating to the reference sample S, the average strength $\bar{I}'_1$, $\bar{I}'_2$, and $\bar{I}'_3$ corresponding to respective unknown concentrations $C'_1$, $C'_2$, $C'_3$ of the alloy can be detected by the PM tube 209 and the A/D converter and amplifier 300. These values are recorded in the computer 400. A software equipped in the computer 400 compares the strengths $\bar{I}'_1$, $\bar{I}'_2$, and $\bar{I}'_3$ with the strengths $\bar{I}_1$, $\bar{I}_2$, and $\bar{I}_3$ and calculates values of respective concentrations $C'_1$, $C'_2$, and $C'_3$. Thus, the kinds and the concentrations of elements to be determined can be found.

According to the provision of a spectrometer of the present invention, only one PM tube is used no matter how many kinds of mineral elements are in a sample to be measured. It is also possible to provide a compact and inexpensive spectrometer, in that an inexpensive and compact photo diode is used as a detector in accordance with the present invention. In addition, the number of peripheral circuits which is needed in the prior art is decreased, thereby enabling the apparatus to be improved in terms of the production and the economy.

Having described the preferred embodiments of the present invention, those skilled in the art having the benefit of the description and drawings can readily devise other modifications and embodiments which are to be considered to be within the scope of the appended claims.

What is claimed is:

1. An apparatus for determining concentrations of mineral elements which comprises:
   a glow discharge lamp having a first window for atomizing and exciting the mineral elements to be measured so as to emit a light through the first window,
   a combined vacuum maintaining device and argon gas supply system for maintaining a vacuum condition in and supplying argon gas to the interior of the glow discharge lamp,
   a high voltage supply member for supplying a high voltage to the glow discharge lamp,
   a spectrometer operatively associated with said glow discharge lamp, said spectrometer including:
      a first focusing lens disposed on an inlet slit for directly focusing the light emitted from the glow discharge lamp through a second window disposed in the spectrometer,
      a laser beam generator in the vicinity of said first focusing lens for generating a laser beam,
      a second focusing lens in the vicinity of said laser beam for directly focusing the laser beam generated from the laser beam,
      a rotary polyhedron disposed in said spectrometer, said rotary polyhedron containing:
         a rotary grating for diffracting a light focused from the first focusing lens,
         a first reflecting mirror for reflecting the laser beam generated from the laser beam through the second focusing lens, and
         a drive motor for driving the rotary polyhedron,
      a second reflecting mirror in the vicinity of rotary polyhedron for reflecting alight diffracted from the rotary grating of the rotary polyhedron, said second reflecting mirror provided with inlet and outlet slits disposed at both sides thereof for reflecting a light diffracted from the grating and the second reflecting mirror, respectively,
      a photomultiplier tube detecting a light reflected from the second mirror and determining a strength of the light,
      a slit plate having a plurality of slits arranged in a circular configuration position for allowing to pass the laser beam reflected from the first reflecting mirror therethrough,
      a plurality of photo diodes in the vicinity of the corresponding slits of said slit plate for analyzing a wavelength and detecting the wavelength of the light diffracted from the second mirror,
      an indicating slit adjacent to said plurality of photo diodes for indicating an initiating point of scanning of the laser beam, and
      a sensing photo diode adjacent to said indicating slit for sensing initiating point of scanning of the laser beam,
   a combined amplifier and A/D converter operatively associated with said spectrometer for amplifying an electric signal from the photomultiplier tube of the spectrometer and converting said amplified signal into a digital signal,
   an amplifier operatively associated with said spectrometer for amplifying signals from the plurality of photo diodes, and
   a computer associated with said spectrometers, digital amplifier and A/D converter, and amplifier for receiving signals transmitted from the digital amplifier and A/D converter, whereby the apparatus can easily measure the concentrations of mineral elements of an alloy.

2. The apparatus in accordance with claim 1, wherein the laser beam generator is a semiconductor laser beam generator.

3. The apparatus in accordance with claim 1, wherein the rotary grating is a hologram grating.

4. The apparatus in accordance with claim 1, wherein one light axis of an optical system focusing the laser beam and the other light axis of an optical system focusing the light to be measured are spaced at a certain angle therebetween so that one light axis cannot meet the other light axis.

5. The apparatus in accordance with claim 1, wherein a central point of the first reflective mirror becomes a center of curvature of the slit plate.

* * * * *